(12) United States Patent
Hille et al.

(10) Patent No.: US 12,285,488 B2
(45) Date of Patent: Apr. 29, 2025

(54) ORAL DOSAGE FORM CONTAINING THEOBROMINE-FREE COCOA

(71) Applicant: LTS LOHMANN THERAPIE-SYSTEME AG, Andernach (DE)

(72) Inventors: Thomas Hille, Neuwied (DE); Gabriel Wauer, Ahrweiler (DE); Frank Seibertz, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 310 days.

(21) Appl. No.: 16/977,018

(22) PCT Filed: Mar. 1, 2018

(86) PCT No.: PCT/EP2018/055105
§ 371 (c)(1),
(2) Date: Aug. 31, 2020

(87) PCT Pub. No.: WO2019/166098
PCT Pub. Date: Sep. 6, 2019

(65) Prior Publication Data
US 2021/0000963 A1    Jan. 7, 2021

(51) Int. Cl.

| | | |
|---|---|---|
| A61K 47/46 | (2006.01) | |
| A61K 9/00 | (2006.01) | |
| A61K 31/4178 | (2006.01) | |
| A61K 31/4196 | (2006.01) | |
| A61K 31/465 | (2006.01) | |
| A61K 47/02 | (2006.01) | |
| A61K 47/10 | (2017.01) | |
| A61K 47/18 | (2017.01) | |
| A61K 47/26 | (2006.01) | |
| A61K 47/32 | (2006.01) | |
| A61K 47/38 | (2006.01) | |

(52) U.S. Cl.
CPC ............ *A61K 47/46* (2013.01); *A61K 9/0053* (2013.01); *A61K 31/4178* (2013.01); *A61K 31/4196* (2013.01); *A61K 31/465* (2013.01); *A61K 47/02* (2013.01); *A61K 47/10* (2013.01); *A61K 47/186* (2013.01); *A61K 47/26* (2013.01); *A61K 47/32* (2013.01); *A61K 47/38* (2013.01)

(58) Field of Classification Search
CPC .............. A61K 31/4178; A61K 31/465; A61K 47/10; A61K 47/186; A61K 47/26; A61K 47/32; A61K 47/38
See application file for complete search history.

(56) References Cited

U.S. PATENT DOCUMENTS

| | | | |
|---|---|---|---|
| 1,851,872 A | 3/1932 | Schreiber et al. | |
| 1,947,717 A | 2/1934 | Kellogg et al. | |
| 2,118,129 A | 5/1938 | Zenlea et al. | |
| 2,275,835 A | 3/1942 | Balmert et al. | |
| 4,242,323 A | 12/1980 | Vlock | |
| 4,390,698 A * | 6/1983 | Chiovini | C07D 473/04 426/431 |
| 4,444,798 A | 4/1984 | Magnolato et al. | |
| 4,670,444 A | 6/1987 | Grohe et al. | |
| 2003/0087937 A1 | 5/2003 | Lindberg | |
| 2014/0333003 A1 | 11/2014 | Allen et al. | |

FOREIGN PATENT DOCUMENTS

| | | | |
|---|---|---|---|
| CA | 2185690 A1 | 3/1995 | |
| CN | 103583781 B | 11/2015 | |
| DE | 000069505361 * | 6/1999 | ........... A61K 9/0056 |
| DE | 69505361 T2 | 6/1999 | |
| EP | 0066700 A1 | 12/1982 | |
| ES | 2105970 A1 | 10/1997 | |
| WO | 9524890 A1 | 9/1995 | |
| WO | 0182714 A1 | 11/2001 | |
| WO | WO-2004084865 A1 * | 10/2004 | ............. A61K 31/00 |
| WO | 2004012702 A1 | 12/2004 | |
| WO | 2008140371 A1 | 11/2008 | |

OTHER PUBLICATIONS

Time Stark, Sabine Bareuther, Thomas Hofmann, Molecular Definition of the Taste of Roasted Cocoa Nibs (*Theobroma cacao*) by Means of Quantitative Studies and Sensory Experiments, Jun. 2006, Journal of Agricultural and Food Chemistry, 54, 5530-5539 (Year: 2006).*
Kaur. International Journal of Pharmaceutics 529, 2017, 134-160 (Year: 2017).*
Miller (Diabetes Care vol. 12, No. 1, Suppl. 1, Jan. 1989 (Year: 1989).*
Shahmohammadi. Biotech Health Sci. Aug. 2016; 3(3):e35084 (Year: 2016).*
Karki. Asian Journal of Pharmaceutical Sciences 11, 2016, 559-574 (Year: 2016).*
Sohi, Drug Development and industrial Pharmacy, vol. 30, No. 5, pp. 429-448, 2004 (Year: 2004).*
Gene A. Siller , "Caffeine", Health Research and Studies Center and Shero Foundation, Los Altos, California, 1998, 6 pages.
XP-002786898; BIOSIS; Molecular definition of the taste of roasted cocoa nibs (*Theobroma cacao*) by means of quantitative studies and sensory experiments, 2 pages; 2017.
Office Action for Japanese Application No. 2020-545561, Dated Nov. 2, 2021, 5 pages.
Office Action for European Application No. 18 709 516.1 dated Feb. 9, 2023, 5 pages.

* cited by examiner

*Primary Examiner* — Susanna Moore
*Assistant Examiner* — Luisalberto Gonzalez
(74) *Attorney, Agent, or Firm* — Lippes Mathias LLP

(57) ABSTRACT

Disclosed are stable dosage forms for oral administration of active pharmaceutical ingredients in which any unpleasant taste sensation, caused by release of the active pharmaceutical ingredient and/or of the excipients in the oral and pharyngeal cavity of the patient, is masked by the use of theobromine-free cocoa.

14 Claims, No Drawings

ORAL DOSAGE FORM CONTAINING THEOBROMINE-FREE COCOA

SUBJECT MATTER OF THE APPLICATION

The present invention relates to dosage forms for oral administration of active pharmaceutical ingredients in which any unpleasant taste sensation is masked by the addition of theobromine-free cocoa. The mentioned dosage forms are dosage forms which release the active ingredient in the oral and pharyngeal cavity. The taste sensations to be masked are due to one or more active pharmaceutical ingredients, one or more excipients, or a combination of active pharmaceutical ingredient(s) with excipient(s).

PRIOR ART

In addition to oral medicaments such as tablets or capsules, which are swallowed whole and release the active ingredient in the gastrointestinal tract, there also exist dosage forms suitable for oral administration in which the contained active ingredient is already released in the oral and pharyngeal cavity and is then swallowed and absorbed in the gastrointestinal tract, or is already, before that, partially or completely absorbed through the oral mucosa.

These dosage forms are used particularly for patients who have difficulty swallowing dosage forms such as tablets or capsules, which may include geriatric and paediatric patients. Dosage forms in which the active ingredient is already absorbed through the oral mucosas have the further advantage that the liver passage and the metabolism of the active ingredient taking place there are avoided. A reduced therapeutic effect possibly associated therewith and increased side effects are thus prevented. In addition, absorption through the oral mucosas leads to a faster onset of action in comparison to dosage forms in which the active ingredient is only absorbed once in the gastrointestinal tract. Such dosage forms are used particularly for the treatment of cancer patients, for the suppression of vomiting during chemotherapy, and for smoking cessation, since this is where a rapid onset of action is particularly desirable.

The products SetoFilm®, Breakyl® and NiQuitin Strips® are examples of products that offer the above-mentioned advantages. Breakyl®, a buccally applicable film containing the opioid fentanyl, dissolves in the oral cavity within 15 to 30 minutes after administration, during which time the active ingredient can be absorbed into the oral mucosa. The oral film SetoFilm® is placed on the tongue, where it dissolves within seconds. The active ingredient is swallowed together with the saliva and is absorbed in the gastrointestinal tract. NiQuitin Strips®, which are orally ingested films, dissolve in the oral cavity within three minutes. The active ingredient, nicotine, is partly absorbed through the mucosas and partly also gastrointestinally after swallowing.

However, the release of the active ingredient in the oral and pharyngeal cavity of the patient may be associated with the occurrence of an unpleasant taste, depending on the active ingredient in question. It has been known for centuries that many active ingredients may have an unpleasant, bitter taste (see Heinrich Hoffmann; Der Struwwelpeter, 1st edition 1846, page 5: "And the doctor sits there and gives him bitter medicine"). Especially in children, this reduces compliance and thus the success of the therapy. But also in cancer patients a decrease in compliance may be observed due to a negative taste sensation when ingesting the drug in spite of the enormous toll of chemotherapy (for example in the case of the above-mentioned SetoFilm®).

Particular attention must therefore be paid in the formulation development of these dosage forms in order to avoid an unpleasant taste sensation that may be caused by the active pharmaceutical ingredient(s), excipient(s), or combinations thereof during administration.

Whereas, for solid dosage forms that are swallowed whole and release the contained active ingredient in the gastrointestinal tract, taste masking can easily be ensured by a functional coating that ensures that the active ingredient is only released at the site of intended absorption, the challenge with dosage forms that are intended to release the active ingredient already in the oral and pharyngeal cavity is much greater.

Previously known measures to improve the taste of oral pharmaceutical preparations can be divided into the following three groups: a) masking by cognitive deception: addition of sweetening agents and flavourings; b) masking by lowering the concentration of free active ingredient molecules: formation of molecular complexes (including cyclodextrin inclusion compounds), formation of ion exchange complexes, use of another counter ion, formation of non-ionic forms of the active ingredient, filming of the particles in a suspension; c) masking by reducing the receptor contact time: increase in viscosity, use of a lipophilic vehicle, formation of particulate solutions (for example, suspension). A combination of these measures may also be used.

In the case of dosage forms in which the active ingredient is intended to be absorbed through the oral mucosas, however, the measures under b) and c) are out of the question because they significantly reduce the absorption rate of the active ingredients in the oral and pharyngeal cavity. The measures under a) in turn have the disadvantage that the addition of sweet-tasting, fruity ingredients produces an excessively sweet taste, which, for example, tempts children to take medication excessively or unintentionally. It should be noted: "A medicinal product should not taste like candy!". Furthermore, some sweetening agents, such as aspartame, have a bitter aftertaste which is perceived as unpleasant. Others, such as acesulfame potassium in the commercial product Setofilm®, which many patients find unpleasant tasting, are not strong enough to suppress an unpleasant taste.

A prior art method for taste masking in dosage forms which release the active ingredient in the oral cavity is described in patent application WO 2004/012702 A1 of the company Pharmacia. It discloses dosage forms with a rapid onset of action in which the bitter taste of the active ingredient sildenafil is masked in the oral cavity by using cocoa powder. In addition to the taste-masking function, the cocoa powder also acts as a binder and is thus intended to provide a pleasant surface texture for the compositions. The proportion of cocoa powder used in the disclosed formulation examples is 30-70% by weight. In addition to cocoa powder, however, the formulations also contain aspartame as a sweetening agent, as well as vanilla or peppermint flavours.

DE 69505361 discloses chewable tablets containing the active ingredients troxerutin, calcium carbonate, calcium phosphate, arginine aspartate, arginine glutamate, amoxicillin and combinations thereof. To mask the unpleasant taste of these active ingredients, cocoa powder is added to the chewable tablets. It also has the function of a binder in addition to masking the taste. The proportion of cocoa powder in relation to the total mass of the tablet is given as 1 to 50% by weight, preferably 14 to 30% by weight. In the practical examples, the proportion is ultimately 25 to 46% by weight. The formulations also include one or more sweetening agents (aspartame, mannitol, sorbitol) and various flavourings.

US 2003/0087937 A1 describes pharmaceutical preparations for oral administration containing nicotine. The preparations release the active ingredient in the oral cavity, where it is absorbed through the oral mucosa. The bitter taste of the active ingredient is masked by a preferred amount of cocoa powder of 17-50% by weight.

What all of these documents have in common is that the formulations for oral administration disclosed therein have a cocoa powder content of at least 17% by weight and that the cocoa powder acts not only as a taste-masking agent but also as a binder. However, this high proportion of at least 17% by weight of cocoa powder greatly restricts formulation development. With such a high proportion of taste-masking agent, the formulation developer has little freedom of design for other excipients to adequately control other properties of the dosage form, in particular the release profile and stability. In film formulations with a proportion of cocoa powder higher than 15% by weight, for example, increased brittleness of the films occurs, and these therefore do not meet regulatory requirements and cannot be used as a medicament. However, lower amounts of cocoa powder are inadequate to sufficiently mask a negative taste sensation.

There is thus a need for dosage forms in which negative taste sensations are masked by the use of a taste corrector and said taste corrector is present in an amount that does not restrict the formulation development and with which sufficient stability of the dosage form can be guaranteed.

DETAILED DESCRIPTION

Against the background of the aforementioned prior art, the aim of the present invention was to provide stable dosage forms for oral administration of active pharmaceutical ingredients in which any unpleasant taste sensation, caused by release of the active pharmaceutical ingredient and/or excipients in the oral and pharyngeal cavity of the patient, is masked by taste masking.

Surprisingly, the aim was addressed by using theobromine-free cocoa, which masks the unpleasant taste resulting from the active ingredient(s), excipient(s) or combinations thereof.

In contrast to the previously known prior art, taste masking is already achieved at a proportion of less than 15% by weight, and therefore the formulation development is not adversely affected.

In a further aspect of the invention, dosage forms are disclosed which, in addition to theobromine-free cocoa, contain less than 5% by weight of another taste corrector.

In a further aspect, the present invention deals with the production of theobromine-free cocoa which can be used to reduce unpleasant taste sensations in pharmaceutical products.

For better understanding, the terms used in this application are explained in greater detail.

A dosage form is the preparation in which an active pharmaceutical ingredient is applied for therapeutic use. Dosage forms comprises a mixture of pharmaceutical active ingredient(s) and excipients which has been processed in a specific way. The different dosage forms can be classified according to the location of administration. Oral dosage forms are taken by mouth and include, for example, tablets or capsules. These are swallowed and the contained active pharmaceutical ingredient is released and absorbed in the gastrointestinal tract. Other oral dosage forms release the active pharmaceutical ingredient already in the oral and pharyngeal cavity, where it is either swallowed together with the saliva and absorbed in the gastrointestinal tract, or is already absorbed through the mucosas in the oral and pharyngeal cavity—transmucosally. In addition, oral dosage forms are also known which lead to the absorption of the active ingredient at both locations.

Solid dosage forms that release the active pharmaceutical ingredient already in the oral and pharyngeal cavity include the following: chewable tablets, conventional sublingual and buccal tablets, muco-adhesive sublingual and buccal tablets, orodispersibie tablets, oral lyophilisates, oral films, pastilles and lozenges, oral therapeutic systems and chewing gums.

Chewable tablets are tablets that are bitten into in the mouth, chewed, and then swallowed. They are especially suitable for children and patients who cannot or do not want to swallow ordinary tablets.

Conventional sublingual and buccal tablets are deposited under the tongue—sublingual—or between the gums and cheek—buccal. There, the tablets slowly melt and release the active ingredient they contain. Mucoadhesive sublingual and buccal tablets also have incorporated polymers that ensure firm adhesion at the desired application site.

Orodispersible tablets differ from conventional tablets by their very short disintegration time in saliva. According to the European Pharmacopoeia (Ph. Eur.), they should disintegrate within 3 to 8 minutes, according to FDA in up to 30 seconds. In contrast to oral lyophilisates and films, the orodispersible tablets have a high mechanical stability.

Oral lyophilisates, usually also called orally disintegrating tablets, are produced by freeze-drying drug/excipient dispersions as platelets for oral use. Upon contact with small amounts of saliva, they disintegrate within a few seconds and thus release the active pharmaceutical ingredient. The contained active pharmaceutical ingredient is not usually intended to be absorbed through the oral mucosa, but is absorbed in the gastrointestinal tract. However, a certain amount of active ingredient may also be absorbed through the oral mucosa. Lyophilisates are usually applied under the tongue (sublingually) or on the tongue (lingually). In oral films, a distinction is made between orodispersible films (other synonyms are orally disintegrating films, thin strips, wafers) and mucoadhesive films. The former are thin, flexible dosage forms that disintegrate rapidly on contact with saliva in the oral cavity. Mucoadhesive films, on the other hand, adhere to the oral mucosa and release the active pharmaceutical ingredient at the desired application site. Furthermore, they do not dissolve immediately, but retain their shape and mechanical strength for a certain period of time.

Pastilles and lozenges continuously release the contained active pharmaceutical ingredient by sucking.

An example of an oral therapeutic system is the product Actiq®. In this product, the active ingredient fentanyl citrate is incorporated into a water-soluble compacted powder pellet that is fixed to the end of a rod-shaped plastic applicator. The patient moves the pellet back and forth using the applicator on the inside of the cheek. The pellet dissolves and quickly releases the fentanyl, which is absorbed through the oral mucosa.

Other solid or semi-solid dosage forms are also conceivable, such as active-ingredient-containing gels that are ingested orally and release the active pharmaceutical ingredient in the oral and pharyngeal cavity. In chewing gums, the contained active pharmaceutical ingredient is released by chewing and then absorbed through the oral mucosas.

An active pharmaceutical ingredient is defined as the pharmacologically active ingredient in a dosage form that is responsible for its therapeutic effect.

Excipients have no therapeutic effect and are necessary so that an active ingredient to be processed into a pharmaceutical form, administered, and absorbed by the body. The various excipients used in pharmaceuticals are classified according to their function; examples of such excipient classes are disintegrants, binders, solvents, fillers, emulsifiers, solubilisers, buffers, antioxidants, preservatives, taste correctors, absorption accelerators, and film formers.

Taste correctors or, used synonymously, taste-masking agents are excipients that improve the taste of a dosage form by masking or covering up an unpleasant taste. They include, for example, sweetening agents and flavourings. The sweetening agents are in turn subdivided into sugars, sugar substitutes, and sweeteners. Sugar substitutes include, for example, the sugar alcohols glucitol, mannitol, maltitol and xylitol as well as fructose. Sweeteners include, amongst other things, sucrose, acesulfame-K, sodium cyclamate, glycyrrhizin, aspartame, dulcin, saccharin, stevioside, naringin dihydrochalcone, aspartame-acesulfame salt, sucralose, monellin, thaumatin, neohesperidine dihydrochalcone and neotame.

Essential oils are also used as taste correctors. Essential oils include lipophilic, volatile plant ingredients such as peppermint oil, lavender oil and chamomile oil. Menthol, the ingredient of peppermint oil, is also used as a flavour corrector.

Examples of flavourings are natural or synthetically produced aromas and essences with the taste of: mint, lemon, orange, peppermint, eucalyptus, apple, cherry, strawberry, pineapple, caramel, tutti-frutti, honey, fruit salad, orange, tangerine, raspberry, coconut, cocoa, vanilla, aniseed, geraniol, almond, honey, liquorice or mixtures thereof.

Taste sensations are individually distinguishable. In principle, a distinction is made between five basic tastes: sweet, salty, umami, sour and bitter. While, in general, the last two especially are perceived as unpleasant, the others may also occur to an extent that is perceived as unpleasant and should therefore be avoided.

The following are known to be unpleasant-tasting active ingredients:
acetaminophen, adlupulon, agomefatine, albuterol, alverine, amitriptyline, amoxicillin, amphetamine sulfate, amygdalin D, apomorphine, arginine aspartate, arginine glutamate, artemisinin, aspirin, atorvastatin, atropine, azathioprine, barbiturates (amobarbital, cyclobarbital, pentobarbital, phenobarbital), benzaldehyde, benzamine, benzoin, brucine, caffeine, calcium carbonate, calcium phosphate, caprolactam, carisoprodol, cascarillin, catechin, cetirizine, quinidine, quinine, chlordiazepoxide, chlorhexidine, chloroquine, chlorpheniramine maleate, chlorpromazine, cinnamedrine, cinchonine, clarithromycin, clobutinol, clonixin, codamine, codeine, colchicine, cycloheximide, deferiprone, demerol, dexamethasone, dextromethorphan, diclofenac, diphenhydramine, diphenylhydantoin, dorzolamide, doxepin, doxylamine, enalapril, epinephrine, erythromycin, falcarindiol, famotidine, fentanyl citrate, glimepiride, guaifenesin, haloperidol, hydrocortisone, ibuprofen, lidocaine, lincomycin, lomotil, loperamide, lupolone, methacholine, methadone, 6-methyl-2-thiouracil, miconazole, morphine hydrochloride, sodium benzoate, neostigmine, nicotine, omeprazole, ondansetron, orphenadrine, pantoprazole, papaverine, pemirolast, penicillin, peroxide, phenacetin, phenothiazine, phenytoin, prednisolone, prednisolone sodium phosphate, prednisone, propylthiouracil, pseudoephedrine hydrochloride, rizatriptan, salicylamide, salicylic acid, salsalate, sildenafil citrate, streptomycin, sulfonamide, terfenadine, topiramate, tramadol, trapidil, trimethadione, trimethoprim, troxerutin, valpromide, vitamins (thiamine), warfarin, and salts thereof.

Furthermore, the following natural ingredients used as active pharmaceutical ingredients are known to have an unpleasant taste:
arbutin, coumarin, cucurbitacin B, ginkgolide A, ginkgolide B, ginkgolide C, harman, helenalin, helicin, humulone, lupinine, noscapine, parthenolide, picrotoxinin, taurine.

The following excipients are known to have an unpleasant taste: acesulfame-K, magnesium sulfate, polysorbates (polysorbate 20, polysorbate 60, polysorbate 80), saccharin.

Other active pharmaceutical ingredients and excipients not listed here may also lead to tastes that are subjectively perceived as unpleasant.

Cocoa is understood to mean the finely ground product obtained from the processed seeds of the cocoa tree and used as a raw material for the production of chocolate and chocolate products and cocoa drinks. When the cocoa fruits are harvested, the fully ripe fruits are cut from the tree. The cocoa seeds are removed from the shell together with the fruit pulp and are subjected to a fermentation process lasting several days. During fermentation, various hydrolytic and enzymatic reactions take place, which are important for the quality of the cocoa beans, especially for the cocoa aroma. The ingress of atmospheric oxygen oxidises and polymerises the polyphenols occurring, thus producing condensed tannins and the phiobaphenes responsible for the brown colour of the cocoa. The fermented beans are dried in the sun or in dryers to a water content of <8% and are freed of foreign matter. During subsequent roasting, the water content drops to 2.5-3%. Acetic acid, acetic acid esters and other undesirable aromatic ingredients are removed and the microbial load is reduced. After cooling, the roasted beans are broken up into cocoa particles and the shells and sprout roots are removed. The cocoa kernels are then crushed and ground to produce the homogeneous, flowable cocoa mass. The broken cocoa kernels can then be broken down under alkaline conditions. The breakdown causes the starch to swell, the acidic components are neutralised, and the cell structure is loosened. The cocoa mass thus broken down contains, just like normal cocoa mass, 52-58% cocoa butter. Alternatively, an alkaline breakdown of the cocoa mass or of the cocoa press cake is carried out. To produce cocoa powder from the cocoa mass, part of the fat is pressed under high pressure. The resulting rock-hard cocoa press cake is then ground into cocoa powder. According to the German Ordinance on Cocoa and Chocolate Products (Kakaoverordnung KakaoV 2003), a distinction is made, depending on the fat content, between cocoa powder with at least 20% cocoa butter content and heavily deoiled or low-fat cocoa powder with less than 20% cocoa butter content in relation to the dry mass.

Theobromine is the chemical compound 3,7-dimethylxanthine-3,7-dihydro-3,7-dimethyl-1H-purine-2,6-dione and the main alkaloid of cocoa. Together with the polyphenols contained in cocoa and the piperazine diones produced during the roasting process, theobromine is responsible for the typically bitter taste of cocoa. In cocoa beans, theobromine is present to an extent of 1.0-2.5% by weight, in cocoa powder to an extent of 1.4-3.0% by weight, and in cocoa shells to an extent of 1.3-2.1% by weight.

Compared to pure theobromine, cocoa only produces an interesting bitter taste sensation. This is due to the fact that other ingredients in cocoa mask the bitter taste of theobromine. In the context of this patent application, theobromine-free cocoa is understood to be cocoa from which at least 80%, preferably at least 90%, most preferably at least 95% of the naturally contained theobromine has been removed by extraction. If the theobromine content of the starting material (cocoa beans, cocoa shells or cocoa powder) is in the range of 1-3% by weight, this results in a theobromine content of at most 0.6% by weight, preferably at most 0.3% by weight, especially preferably at most 0.15% by weight of the theobromine-free cocoa.

The extraction of theobromine from cocoa powder, cocoa beans or cocoa shells can be achieved with milk of lime. Alternatively, the theobromine can also be extracted from the above-mentioned starting materials using supercritical carbon dioxide ($CO_2$).

Theobromine-free cocoa contains theobromine in a proportion of less than 0.6% by weight, preferably less than 0.3% by weight, especially preferably less than 0.15% by weight. The cocoa contains theobromine in a proportion of less than 0.6% by weight, preferably less than 0.3% by weight, especially preferably less than 0.15% by weight.

According to an embodiment of the invention, the oral dosage forms are characterised in that the theobromine-free cocoa contains less than 0.6% by weight of theobromine, preferably less than 0.3% by weight of theobromine, especially preferably less than 0.15% by weight of theobromine.

EXAMPLES

Example 1

Production of Theobromine-Free Cocoa 6 pipes with an internal volume of approx. 6 l are each fed with approx. 1 kg cocoa beans (alternatively, cocoa powder or cocoa shells can also be used). In each case, 3.5 l of drinking water and milk of lime from 100 g of quicklime are poured into the beans in the first two pipes, and the mixtures are stirred well with a glass rod and filtered after a standing time of 12 hours. The filtrates are combined in a 50 l round-bottom flask. The residues are returned to pipes 1 and 2, where they are again mixed each with 3.5 l of water, but milk of lime is reduced to 10 g of quicklime per pipe. The mixtures are stirred well again with a glass rod and filtered after 12 hours of standing time. The filtrate is poured into the 50 l flask. The residues are returned again to the pipes 1 and 2 and again mixed each with 3.5 l of water, and milk of lime reduced to 10 g of quicklime is used per pipe. The combined filtrates are transferred to the fresh beans in pipes 3 and 4, which are mixed with milk of lime made from 100 g of quicklime per pipe, stirred, and filtered after a standing time of 12 hours. The extraction of theobromine is continued for pipes 5 and 6. In the first extraction, per pipe, 3.5 l of drinking water and milk of lime from 100 g of quicklime are used, but in the second and third extraction 3.5 l of drinking water and milk of lime from 10 g of quicklime are used per pipe.

All filter residues are combined and dried to prevent mould formation.

This results in approx. 40 l of a brown solution, which contains water-soluble calcium theobromate in addition to resins and violet dye. This solution is reduced to approx. 1 l under vacuum. Then, 1 N hydrochloric acid is added until a pH value of about 8 is reached. Carbon dioxide gas is introduced from a steel cylinder or carbonic acid cartridge until the light-yellow theobromine is completely precipitated from the solution. After 12 hours, the filter residues mentioned above, i.e. the theobromine-free cocoa beans, are funneled off and combined with the filtrate, which is then concentrated in a vacuum until dry.

After drying, the beans are pulverised in a cross beater mill. The result is theobromine-free cocoa, which is used for further experiments.

Example 2

Production of Theobromine-Free Cocoa
(Alternative Method)

100 g of commercial cocoa shells from the company Caelo, Ch.-B.: 14096914 (alternatively cocoa beans or cocoa powder can be used), were slurried in 310 g 10% calcium oxide suspension and 300 g water and left to stand overnight. After suctioning off and washing with a little water, the residue was suspended in 100 g 10% calcium oxide suspension and 600 g water and left to stand overnight. It was suctioned off again and the residue was slurried in 500 g of water. After suctioning the residue had a distinct white coating of calcium oxide or calcium hydroxide. The residue was therefore slurried in 100 g conc. HCl and 500 g water, suctioned off, and washed with water until the filtrate was pH-neutral. The residue was brown without a white coating. The residue was dried in a circulating air cabinet at 100-120° C. A part was ground in a coffee grinder.

In the first three filtrates, theobromine could be detected by thin-layer chromatography (mobile phase: methylene chloride:ethanol:acetic acid 88:10:2, plate: silica gel 60F254; detection: UV).

Example 3 (Comparative Examples with the Active Ingredient Ondansetron)

Different film formulations with different proportions of cocoa were produced. The taste of the oral films produced was then evaluated by a group of test subjects. With the exception of the addition of cocoa, the formulations corresponded to the formulation of the commercial product Setofilm®, published in, amongst others, WO 2008/040534 (page 29, Table 1).

Preparation of Formulations 3.1, 3.2 and 3.3
a) First, water is provided and heated; polyethylene glycol 1000 and polyvinyl alcohol 4-88 are added while stirring and are stirred until completely dissolved.
b) Then, rice starch, ondansetron and ethanol are added and stirred until the mass is homogeneous.
c) Then, titanium dioxide, glycerol, cocoa, acesulfame-K, menthol and polyoxyethylene sorbitan monooleate are added and stirred until homogeneous.
d) The mass is spread as a thin film on a process film and dried for 15 minutes at 50° C.
e) The dry film is separated.

TABLE 1

Film formulations containing ondansetron and cocoa powder.

| | Composition of the oral films (in % by weight) | | |
|---|---|---|---|
| | 3.1 | 3.2 | 3.3 |
| Ondansetron | 15.84 | 15.84 | 15.84 |
| Polyvinyl alcohol 4-88 | 40.13 | 36.69 | 33.26 |
| Polyethylene glycol 1000 | 11.88 | 11.88 | 11.88 |
| Glycerol | 3.96 | 3.96 | 3.96 |
| Rice starch | 18.24 | 16.68 | 15.11 |
| Acesulfame-K | 0.4 | 0.4 | 0.4 |
| Titanium dioxide | 0.6 | 0.6 | 0.6 |

TABLE 1-continued

Film formulations containing ondansetron and cocoa powder.

| | Composition of the oral films (in % by weight) | | |
|---|---|---|---|
| | 3.1 | 3.2 | 3.3 |
| Menthol | 1.98 | 1.98 | 1.98 |
| Polyoxyethylene sorbitan monooleate | 1.98 | 1.98 | 1.98 |
| Cocoa | 5.00 | 10.00 | 15.00 |
| Σ | 100.0 | 100.0 | 100.0 |

A taste test in a small group of test subjects showed that a taste-masking effect of cocoa is only present in formulation 3.3, which contains a cocoa proportion of 15% by weight. During the production of films with a higher cocoa content, the film broke.

Example 4 (Formulations According to the Invention Containing the Active Ingredient Ondansetron)

Formulations of oral films containing ondansetron were prepared. The formulations corresponded to the formulation of the commercial product Setofilm® with the exception that instead of the sweetening agent acesulfame K and the flavouring menthol, theobromine-free cocoa was contained.

Production of Formulations 4.1, 4.2 and 4.3 a) First, water is provided and heated; polyethylene glycol 1000 and polyvinyl alcohol 4-88 are added while stirring and are stirred until completely dissolved.

b) Then, rice starch, ondansetron and ethanol are added and stirred until the mass is homogeneous.

c) Then, titanium dioxide, glycerol, theobromine-free cocoa and polyoxyethylene sorbitan monooleate are added and stirred until homogeneous.

d) The mass is spread as a thin film on a process film and dried for 15 minutes at 50° C.

e) The dry film is separated.

The individual formulations were produced with the compositions listed in Table 2 and were subjected to taste testing by a group of test subjects.

TABLE 2

Film formulations containing ondansetron and theobromine-free cocoa powder.

| | Composition of the oral films (in % by weight) | | |
|---|---|---|---|
| Component | 4.1 | 4.2 | 4.3 |
| Ondansetron | 15.84 | 15.84 | 15.84 |
| Polyvinyl alcohol 4-88 | 41.51 | 38.07 | 34.64 |
| Polyethylene glycol 1000 | 11.88 | 11.88 | 11.88 |
| Glycerol | 3.96 | 3.96 | 3.96 |
| Rice starch | 19.24 | 17.68 | 16.11 |
| Titanium dioxide | 0.6 | 0.6 | 0.6 |
| Polyoxyethylene sorbitan monooleate | 1.98 | 1.98 | 1.98 |
| theobromine-free cocoa | 5.00 | 10.00 | 15.00 |
| Σ | 100.0 | 100.0 | 100.0 |

Already, formulation 4.1, which contains 5% by weight of theobromine-free cocoa, masks the unpleasant, bitter taste of the active ingredient ondansetron.

Example 5 (Formulations With the Active Ingredient Nicotine)

The oral films were produced as in Example 4.

| | Composition of the oral films (in % by weight) | |
|---|---|---|
| Component | 5.1 (comparative example) | 5.2 (example according to the invention) |
| Nicotine | 3.75 | 3.75 |
| Methacrylic acid - ethyl acrylate copolymer (1:1) Type A | 46.38 | 46.38 |
| Triethyl citrate | 23.92 | 23.92 |
| Peppermint flavour TAK-032230 | 9.96 | 9.96 |
| Sucralose USP/NF | 2.00 | 2.00 |
| Sodium hydrogen carbonate | 3.99 | 3.99 |
| Cocoa | 10.00 | |
| Theobromine-free cocoa | | 10.00 |
| Σ | 100.0 | 100.0 |

The mass is spread as a thin film on a process film and dried for 15 minutes at 50° C. The dry film is then separated.

Example 6 (Formulations Containing the Active Ingredient Rizatriptan)

The oral films were produced as in Example 4.

| | Composition of the oral films (in % by weight) | | | |
|---|---|---|---|---|
| Component | 6.1 (comparative example) | 6.2 (comparative example) | 6.3 (inventive example) | 6.4 (inventive example) |
| Rizatriptan benzoate USP | 17.129 | 15.326 | 17.129 | 15.326 |
| Copovidone NF | 5.187 | 4.641 | 5.187 | 4.641 |
| Hydroxypropyl cellulose LF USP/EP | 61.779 | 55.276 | 61.779 | 55.276 |
| Butylhydroxytoluene USP/EP | 0.010 | 0.009 | 0.010 | 0.009 |
| Ammonium glycyrrhizate EP | 0.523 | 0.468 | 0.523 | 0.468 |
| Sucralose USP/NF | 1.036 | 0.927 | 1.036 | 0.927 |
| Titanium dioxide USP/EP | 1.558 | 1.394 | 1.558 | 1.394 |

| Component | 6.1 (comparative example) | 6.2 (comparative example) | 6.3 (inventive example) | 6.4 (inventive example) |
|---|---|---|---|---|
| Menthol USP/EP | 1.036 | 0.927 | 1.036 | 0.927 |
| Triacetin USP | 6.745 | 6.035 | 6.745 | 6.035 |
| Cocoa | 5.000 | 15.000 | | |
| Theobromine-free cocoa | | | 5.000 | 15.000 |
| Σ | 100.0 | 100.0 | 100.0 | 100.0 |

The mass is spread as a thin film on a process film and dried for 15 minutes at 50° C. The dry film is then separated.

The invention claimed is:

1. An oral dosage form in the form of an oral film which, when administered, releases an active pharmaceutical ingredient into the oral and pharyngeal cavity, said oral dosage form containing:
   a) at least one active pharmaceutical ingredient;
   b) at least one excipient; and
   c) theobromine-free cocoa, wherein the oral dosage form contains at most 10% by weight of theobromine-free cocoa.

2. The oral dosage form according to claim 1, characterised in that the dosage form contains at most 5% by weight of theobromine-free cocoa.

3. The oral dosage form according to claim 1, characterised in that the dosage form contains at least 2% by weight of theobromine-free cocoa.

4. The oral dosage form according to claim 1, characterised in that the dosage form contains less than a total of 5% by weight of one or more further taste correctors.

5. The oral dosage form according to claim 4, characterised in that the taste correctors are sweetening agents and/or flavourings.

6. The oral dosage form according to claim 1, characterised in that the theobromine-free cocoa contains less than 0.6% by weight of theobromine.

7. The oral dosage form according to claim 1, characterised in that the active pharmaceutical ingredient is present in the dosage form in a content which, without the use of a taste corrector, leads to an unpleasant taste sensation when ingested.

8. The oral dosage form according to claim 1, characterised in that the active pharmaceutical ingredient is present in a content of at least 2% by weight and at most 20% by weight.

9. The oral dosage form according to claim 1, characterised in that the excipient or excipients are selected from the group comprising disintegrants, binders, solvents, fillers, emulsifiers, solubilisers, buffers, preservatives, sweetening agents, flavourings, absorption antioxidants, accelerators, or combinations thereof.

10. A method to mask an unpleasant taste sensation when using oral dosage forms which release at least one active pharmaceutical ingredient in the oral and pharyngeal cavity, said method comprising the administration of the oral dosage form of claim 1.

11. The oral dosage form according to claim 1, characterised in that the theobromine-free cocoa contains less than 0.3% by weight of theobromine.

12. The oral dosage form according to claim 1, characterised in that the theobromine-free cocoa contains less than 0.15% by weight of theobromine.

13. An oral dosage form in the form of an oral film which, when administered, releases an active pharmaceutical ingredient into the oral and pharyngeal cavity, said oral dosage form containing
   a) at least one active pharmaceutical ingredient selected from the group consisting of acetaminophen, adlupulon, agomelatine, albuterol, alverine, amitriptyline, amphetamine sulfate, amygdalin D, apomorphine, artemisinin, aspirin, atorvastatin, atropine, azathioprine, barbiturates, amobarbital, cyclobarbital, pentobarbital, phenobarbital, benzaldehyde, benzamine, benzoin, brucine, caffeine, caprolactam, carisoprodol, cascarillin, catechin, cetirizine, quinidine, quinine, chlordiazepoxide, chlorhexidine, chloroquine, chlorpheniramine maleate, chlorpromazine, cinnamedrine, cinchonine, clarithromycin, clobutinol, clonixin, codamine, codeine, colchicine, cycloheximide, deferiprone, demerol, dexamethasone, dextromethorphan, diclofenac, diphenhydramine, diphenylhydantoin, dorzolamide, doxepin, doxylamine, enalapril, epinephrine, erythromycin, falcarindiol, famotidine, fentanyl citrate, glimepiride, guaifenesin, haloperidol, hydrocortisone, ibuprofen, lidocaine, lincomycin, lomotil, loperamide, lupolone, methacholine, methadone, 6-methyl-2-thiouracil, miconazole, morphine hydrochloride, sodium benzoate, neostigmine, nicotine, omeprazole, ondansetron, orphenadrine, pantoprazole, papaverine, pemirolast, penicillin, peroxide, phenacetin, phenothiazine, phenytoin, prednisolone, prednisolone sodium phosphate, prednisone, propylthiouracil, pseudoephedrine hydrochloride, rizatriptan, salicylamide, salicylic acid, salsalate, sildenafil citrate, streptomycin, sulfonamide, terfenadine, topiramate, tramadol, trapidil, trimethadione, trimethoprim, valpromide, vitamins, thiamine, warfarin, and salts thereof, arbutin, coumarin, cucurbitacin B, ginkgolide A, ginkgolide B, ginkgolide C, harman, helenalin, helicin, humulone, lupinine, noscapine, parthenolide, picrotoxinin, taurine, acesulfame-K, magnesium sulfate and saccharin;
   b) at least one excipient; and
   c) theobromine-free cocoa, wherein the oral dosage form contains at most 15% by weight of theobromine-free cocoa.

14. The oral dosage form according to claim 13, characterized in that the active pharmaceutical ingredient comprises ondansetron, nicotine or rizatriptan.

* * * * *